United States Patent [19]

Oh et al.

[11] Patent Number: 4,971,962

[45] Date of Patent: Nov. 20, 1990

[54] CEPHALOSPORIN COMPOUNDS

[75] Inventors: Hun S. Oh; Yong Z. Kim; Jae H. Yeo; Jong C. Lim; Won S. Kim; Soon H. An, all of Daejeon-Si; Chan S. Bang, PyeongTaek; Hyeon J. Yim, Daejeon-Si, all of Rep. of Korea

[73] Assignee: Lucky, Ltd., Seoul, Rep. of Korea

[21] Appl. No.: 350,617

[22] Filed: May 11, 1989

[30] Foreign Application Priority Data

May 11, 1988 [KR] Rep. of Korea ...................... 88-5447

[51] Int. Cl.[5] .................. C07D 501/36; A61K 31/545

[52] U.S. Cl. .................................... 514/206; 514/207; 540/225; 540/227; 540/228

[58] Field of Search ............... 540/222, 226, 227, 225, 540/221; 514/225, 206, 207

[56] References Cited

FOREIGN PATENT DOCUMENTS 61-189285 8/1986 Japan .

1399086 6/1975 United Kingdom .

*Primary Examiner*—Nicholas S. Rizzo

*Attorney, Agent, or Firm*—Birch, Stewart, Kolasch & Birch

[57] ABSTRACT

The present invention relates to novel cephalosporin compounds having high antimicrobial activity, which are shown by the formula(I), and to a process for preparing them

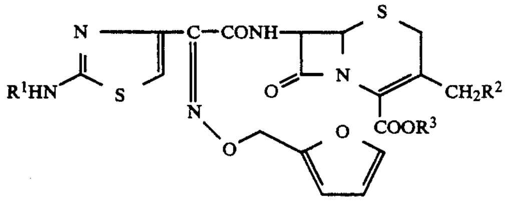

(I)

wherein $R^1$ is a hydrogen atom or an amino protecting group;

$R^2$ is acetoxy; and $R^3$ is a hydrogen atom or a carboxyl protecting group (wherein when $R^2$ contains quaternary ammonium, $R^2$ and $R^3$ may form a zwitter ion).

The present invention also relates to the non-toxic and pharmaceutically acceptable salts of the cephalosporin compounds of the formula (I). Also described are compositions containing the antibiotics according to the present invention.

8 Claims, No Drawings

CEPHALOSPORIN COMPOUNDS

BACKGROUND OF THE INVENTION

The present invention relates to new cephalosporin type compounds which have antimicrobial activities, and to a process for preparation thereof. More particularly, it relates to new cephem derivatives shown by the following formula(I) and pharmaceutically acceptable salts thereof or metabolically labile esters thereof, and to a process for preparing them. This invention also relates to pharmaceutical compositions comprising the new cephem compounds of the formula(I) as active ingredients

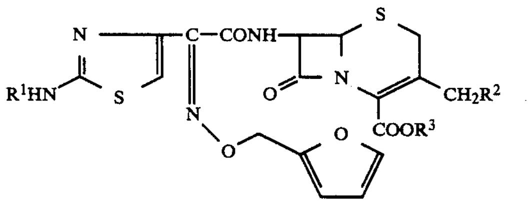
(I)

wherein $R^1$ is a hydrogen atom or an amino protecting group;

$R^2$ is acetoxy, a heterocyclic group, or a sulfur atom linked with a heterocyclic group; and $R^3$ is a hydrogen atom or a carboxyl protecting group (wherein when $R^2$ contains quaternary ammonium, $R^2$ and $R^3$ may form a zwitter ion).

Since the first discovery that cephalosporin derivatives exhibit potent antibiotic activities, a large number of cephalosporin type compounds possessing improved or broad antibiotic activities and high selectivity have been developed (Note, for example, J. Med. Chem. 12, 310(1969); U.S. Pat. No. 3,970,651, etc.). Nowadays, cephalosporin antibiotics are widely used in the treatment of diseases caused by pathogenic bacteria in human beings and animals, and are especially useful in the treatment of diseases caused by bacteria which are resistant to other antibiotics such as penicillin compounds and in the treatment of penicillin sensitive patients. In many instances, it is desirable to employ a cephalosporin antibiotic which exhibits activities against gram-positive and gram-negative bacteria, particularly Pseudomonas.

A number of cephalosporin compounds belonging to a class of 3-substituted or unsubstituted-3-cephem-4-carboxylic acids which contain 2-(2-aminothiazole-4-yl)-2-(substituted or unsubstituted alkoxyimino) acetamido group as shown in the following formula(A) at the 7-position of the cephalsporin nucleus have been known.

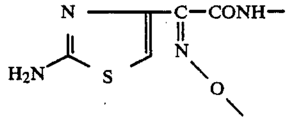
(A)

These antibiotic compounds are characterized by their high antibacterial activities against a range of gram-positive and gram-negative bacteria and particularly high stability of β-lactamase produced by various gram-negative bacteria. Among such cephalosporin compounds, Cefotaxime of the formula(B) (U.S. Pat. No. 4,098,888) and Ceftazidime of the formula(C) (U.S. Pat. No. 4,258,041) are considerably effective in the treatment of diseases caused by general pathogenic bacteria.

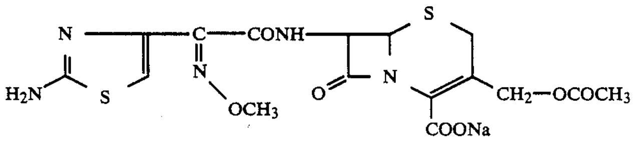
(B)

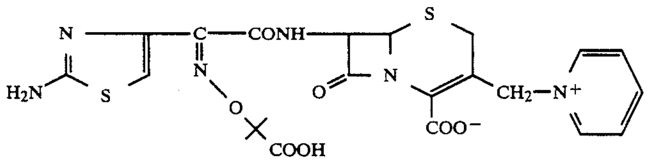
(C)

In GB patent No. 1,399,086, many cephalosporin derivatives which are shown by the formula(D) are described.

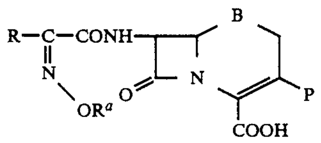
(D)

wherein R is a hydrogen atom or an organic group; $R^a$ is a primary alkyl group to form an ether linkage; B is -S- or

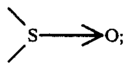

and P is an organic group.

In U.S. Pat. No. 4,278,793, cephalosporin derivatives of the formula (E) are also described,

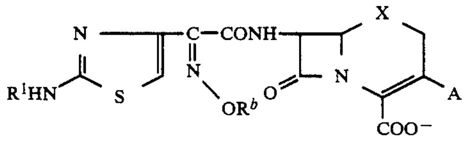
(E)

wherein $R^1$ is a hydrogen atom or an amino protecting group; $R^b$ is a hydrogen atom, an aliphatic group, acyl, aryl, alkoxy, arylsulfonyl or hetero aryl group; X is -S-, -O-,

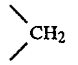 or 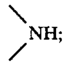

and A is an alkoxy, alkenyloxy group or a halogen atom.

In this way, the cephalosporin derivatives which have 2-(2-aminothiazol-4-yl)-2-(2-furfuryl-oxyimino)-acetamido group at 7-position are first mentioned in the present invention. The cephalsporin are first mentioned in the present invention. The cephalsporin compound of the formula(F) (RN=99951-28-7) which has 2-[2-tri-phenylmethyl)aminothiazol-4-yl]-2-(2-furanylcarbonyloxy imino)-acetamido group at 7-position is also a known compound, but this compound has no correlation with the present invention.

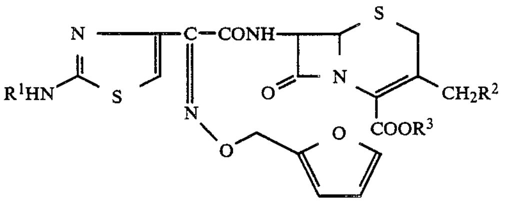

(I)

wherein, $R^1$, $R^2$ and $R^3$ are the same as defined above.

In the formula(I), the amino protecting group of $R^1$ represents a general amino protecting group such as acyl, substituted or unsubstituted ar(lower)alkyl (e.g. benzyl, diphenylmethyl, triphenylmethyl, 4-methoxybenzyl, 3,4-dimethoxybenzyl), halo(lower)alkyl (e.g. trichloromethyl, trichloroethyl, trifluoromethyl), tetrahydropyranyl, substituted phenylthio, substituted alkylidene, substituted aralkylidene or substituted cyclolidene, and the like. The suitable acyl to protect the

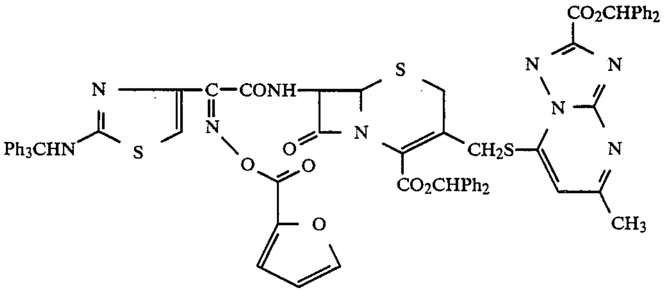

(F)

SUMMARY OF THE INVENTION

An object of the present invention is to provide cephalosporin derivatives of the formula(I), pharmaceutically acceptable salts and metabolically labile esters thereof, and to further provide a process for preparing said derivatives.

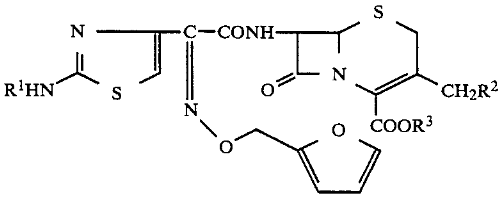

(I)

wherein $R^1$ is a hydrogen atom or an amino protecting group;

$R^2$ is acetoxy, a heterocyclic group, or a sulfur atom linked with a heterocyclic group; and $R^3$ is a hydrogen atom or a carboxyl protecting group (wherein when $R^2$ contains quaternary ammonium, $R^2$ and $R^3$ may form a zwitter ion).

Another object of the present invention is to provide pharmaceutical compositions comprising the cephalosporin derivatives of the formula(I) as active ingredients.

DETAILED DESCRIPTION OF THE INVENTION

The present invention provides cephalosporin derivatives of the formula(I), pharmaceutically acceptable salts thereof and metabolically labile esters thereof amino group includes aliphatic, aromatic or heterocyclic acyl, for example, lower($C_1 \sim C_6$)alkanoyl (e.g. formyl, acetyl, propionyl), $C_2 \sim C_6$ alkoxycarbonyl (e.g. methoxycarbonyl, ethoxycarbonyl, propoxycarbonyl), lower alkanesulfonyl (e.g. methanesulfonyl, ethanesulfonyl), arenesulfonyl (e.g. benzenesulfonyl, p-toluenesulfonyl), aroyl(e.g. benzoyl, toluoyl), ar(lower-)alkanoyl(e.g. phenylacetyl) or ar(lower)alkoxycarbonyl (e.g. benzyloxycarbonyl). Above mentioned acyls may have the $1 \sim 3$ substituents such as halogen(e.g. chlorine, bromine), hydroxy, cyano or a nitro group. Besides, the reaction products of silane, boron or phosphorous compounds with amino group may be attached to the amino protecting group. Especially, triphenylmethyl group is preferred to be used as the amino protecting group, because it can be readily removed under mild conditions.

In the formula(I), $R^2$ represents a heterocyclic group or a sulfur atom linked with a heterocyclic group, and preferably, the former heterocyclic group is, for example, a pydridinium group and the latter heterocylic group is, for example, 1-methyl-1H-tetrazol-5-yl group.

The carboxyl protecting group of $R^3$ includes, for example, lower alkyl esters (e.g. methyl ester, ethyl ester, t-butyl ester), lower alkenyl esters (e.g. vinyl ester, allyl ester), lower alkoxy(lower) alkyl esters(e.g. methoxymethyl ester, ethoxymethyl ester), lower alkylthio(lower)alkyl esters (e.g. methylthiomethyl ester), halo(lower) alkyl esters (e.g. 2,2,2-trichloroethyl ester), substituted or unsubstituted aralkyl esters (e.g. benzyl ester, p-nitrobenzyl ester, p-methoxybenzyl ester), or silyl esters (e.g. trimethylsilyl ester), which can be readily removed under mild conditions. The preferred carboxyl protecting group is p-nitrobenzyl ester or t-butyl ester.

The above mentioned amino protecting group of $R^1$ or carboxyl protecting group of $R^3$ which is readily removed to recover the free amino or carboxyl group under mild conditions such as hydrolysis or reduction, is appropriately selected depending on the chemical properties of the objective compound of the formula(I).

In this specification, the partial structure represented by the following formula

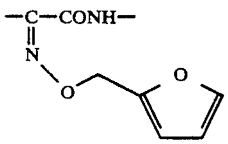

means 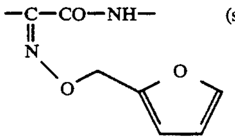 (syn-isomer),

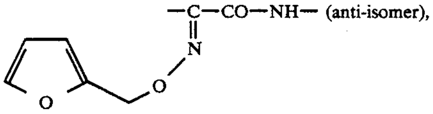 (anti-isomer), or a mixture thereof. Since the syn-isomer is more potent than the anti-isomer in structure-activity relationship, the syn-isomer is more valuable with respect to medical treatment and prevention of disease than the corresponding anti-isomer. According to this invention the compound of the formula(I) is provided in the form of a mixture comprising at least ninety percent of the syn-isomer and the rest of the anti-isomer.

Also, the compounds of the formula(I) according to the present invention may exist in tautomeric forms (for example, in respect of the 2-aminothiazolyl group) and it will be understood that such tautomeric forms, e.g. the 2-iminothiazolinyl form, are included within the scope of the invention.

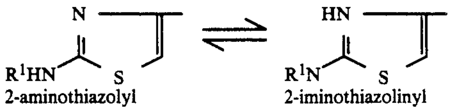

2-aminothiazolyl 2-iminothiazolinyl (wherein $R^1$ is the same as defined above.)

According to another aspect of the invention, a process for preparation of the cephalosporin antibiotics of the formula(I) as hereinbefore defined, is provided. That is, the compounds of the formula(I) can be prepared by a process comprising reacting the activated acylating derivative of the formula(II) with the compound of the formula(III), as shown in [Scheme 1],

[Scheme 1]

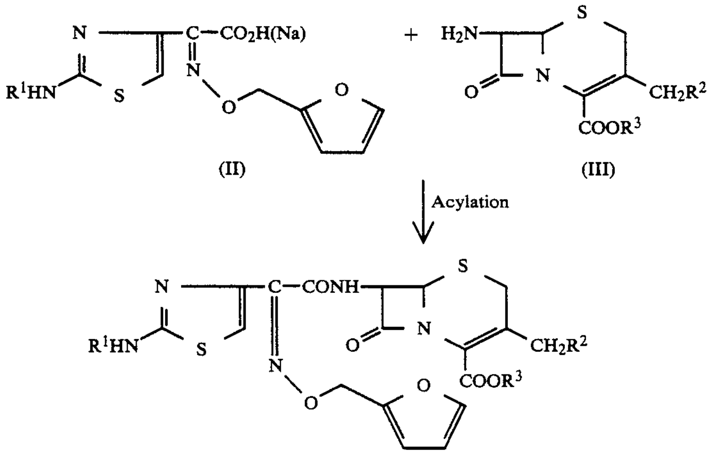

(II) (III) (I)

(wherein $R^1$, $R^2$ and $R^3$ are the same as defined above), and then, if desired, removing the remaining amino protecting group and/or the remaining carboxyl protecting group in a known manner. Suitable examples of the aforesaid activated acylating derivative, that is to say, such activated derivative made reactive at the carboxyl group of the formula(II), include acid halides(e.g. acid chloride), acid anhydrides, mixed acid anhydrides (e.g. acid anhydride derived from reaction with ethylchloro formate, mesitylenesulfonyl chloride, p-toluenesulfonyl chloride or chlorophosphate), or activated esters (e.g. the compound derived from reaction with N-hydroxybenzotriazole in the presence of condensing reagent such as dicyclohexylcarbodiimide). Also, the acylation may be achieved by the free acid of the formula (II) in the presence of condensing reagent such as dicyclohexylcarbodiimide or carbonyl diimidazole. The acylating derivatives of formula(II) used in the present invention include the free acid thereof in the presence of the aforesaid condensing reagent.

Conventional acylation reactions may preferably be achieved in the presence of an organic base such as tertiary amines(e.g. triethylamine, N,N-dimethylaniline, pyridine) or an inorganic base such as sodium bicarbonate, potassium bicarbonate, sodium carbonate and potassium carbonate. In the present invention, the acylation reaction may be conducted in a conventional inert solvent which is selected from the group consisting of halogenated hydrocarbons (e.g. methylene chloride, chloroform), amides (e.g. N,N-dimethylacetamide, N,N-dimethylformamide), tetrahydrofuran, acetonitrile and the like. A particularly preferred solvent is methylene chloride and N,N-dimethylformamide. Also these inert solvents may be used as a mixture with each other or a mixture with water. The foregoing acylation reaction may be carried out at a temperature of −50° to 50° C., preferably −30° to 20° C. The acylating derivative may preferably be used in a stoichiometric amount according to the amount of the compound (III), and in some cases an excess (1.05∼1.20 eq.) may be used.

In the cephalosporin compounds of the formula(I), if desired, the amino protecting group and/or the carboxyl protecting group may be removed from the acylation product by a conventional deprotection technique such as hydrolysis or reduction. And, in case of a compound having an acyl group as the amino protecting group, it is feasible to subject such compound to a reaction with an iminohalogenation reagent and then with an imino-etherification reagent, if necessary, followed by hydrolysis. Acid hydrolysis is one of the conventional methods for removing the amino protecting groups and is applicable to the removal of such groups as tri(di)phenylmethyl or alkoxycarbonyl group. The acids available for this acid hydrolysis may be formic acid, trifluoroacetic acid, p-toluenesulfonic acid, hydrochloric acid, and other organic or inorganic acids, and preferred acids are formic acid and trifluoroacetic acid which afford easy after-treatment of the reaction mixture.

Another process for preparing the compound of the formula(I) is constructed with the acylation reaction of the compound of the formula(II) with the compound of the formula(IV) which has a leaving group at 3-position to give the compound of the formula(V), and then the substitution reaction of the leaving group of the formula(V) with an appropriate substituent, as shown in [Scheme 2],

[Scheme 2]

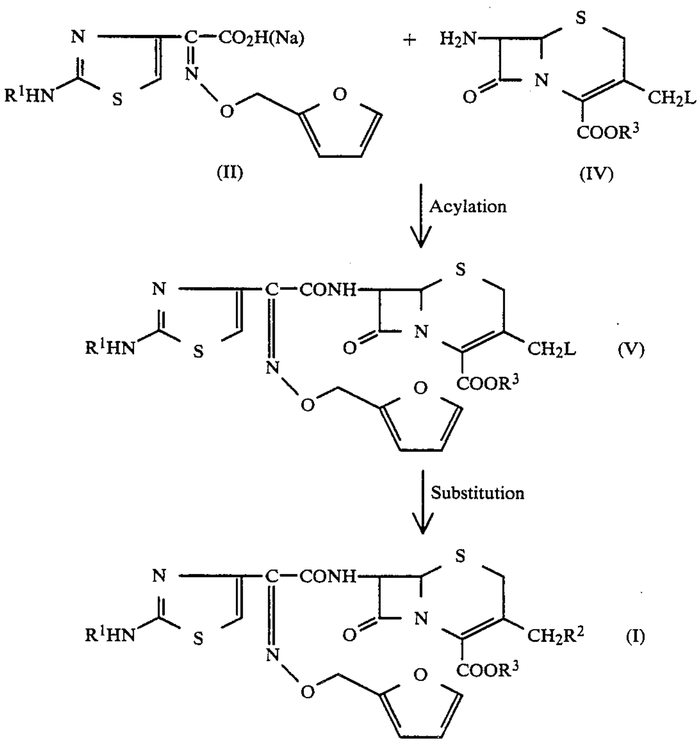

(II) (IV) (V) (I)

wherein $R^1$, $R^2$ and $R^3$ are the same as defined above, L is a leaving group such as a halogen atom (e.g. chlorine, bromine) or acetyloxy group. In the preparation of the compounds of the formula(I) from the compounds of the formula (V), if desired, a catalyst such as sodium iodide and potassium iodide may be used.

The compounds of the formula(II) which are important intermediates employed for the preparation of the new cephalosporin derivatives in accordance with this invention, are also new compounds and may be prepared by a process comprising the following two steps from the compound of the formula(VI), as shown in [Scheme 3],

[Scheme 3]

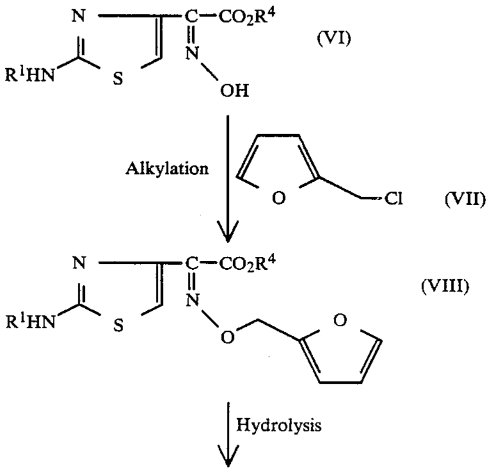

(VI) (VII) (VIII)

-continued

[Scheme 3]

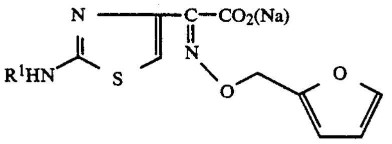

(II)

wherein $R^1$ is a hydrogen atom or an amino protecting group, and $R^4$ is methyl or ethyl group.

The furfuryl chloride shown by the formula(VII) can be obtained by a known method (Ref., Kirner, J. Am. Chem. Soc., 50, 1955 (1928)). The preparation of the formula(VIII) may be conducted in the presence of an inorganic or organic base. Representative inorganic bases may include, for example, alkali metal hydroxides (e.g. sodium hydroxide, potassium hydroxyde), alkali-earth metal hydroxides (e.g. calcium hydroxide), sodium bicarbonate, potassium bicarbonate, sodium carbonate, potassium carbonate and calcium carbonate. Representative organic bases include tertiary amines such as triethylamine. Also the alkylation may be conducted in a conventional inert solvent at a temperature of −20° to 50° C., preferably 0° to 30° C. Examples of the inert solvent are N,N-dimethylformamide, N,N-dimethylacetamide, dimethyl sulfoxide, halogenated hydrocarbons (e.g. methylene chloride), ethers (e.g. tetrahydrofuran), and so on.

The hydrolysis of the compound shown by the formula(VIII) is effected by treatment of the compound with an appropriate base in an inert solvent. Examples of the appropriate base are sodium hydroxide, potassium hydroxide and lithium hydroxide. The inert solvent is ethyl alcohol, methyl alcohol, tetrahydrofuran or a mixture thereof. An aqueous solvent may be used to improve the solubility of the base. The hydrolysis may be conducted at a temperature of −10° to 50° C., preferably 10° to 30° C.

The pharmaceutically acceptable salts of the compounds (I) according to this invention include metal salts such as alkali metal salts (e.g. sodium salt, potassium salt) or alkali-earth metal salts (e.g. magnesium salt, calcium salt), and organic base salts (e.g. ammonium salt, triethylamine salt, pyridine salt, procaine salt), and also include acid salts such as inorganic acid salts (e.g. hydrochloric acid salt, sulfuric acid salt, phosphoric acid salt), organic acid salts (e.g. formic acid salt, acetic acid salt, trifluoroacetic acid salt) or amino acid salts (e.g. lysine salt). Metabolically labile esters of the compounds (I) include acyloxyalkyl esters such as acetoxyethyl, acetoxymethyl and pivaloyloxymethyl esters.

The compounds of the formula(I) in which $R^1$ is hydrogen, exhibit high antibacterial activities against gram-positive and gram-negative bacteria, and are especially useful in the treatment of diseases caused by bacteria in human beings and animals.

In order to illustrate the usefulness of the invented compounds, the minimal inhibitory concentrations (MIC) thereof were compared with one of known compounds such as ceftazidime and moxalactam.

In-vitro antibacterial activity was determined by the two-fold dilution method as described below. 2 μl of the test microorganism which has the $10^7$ CFU per ml was inoculated on the Muller-Hinton agar which has been dispersed by the test compound, and was incubated at 37° C. for 20 hours. The results of the minimal inhibitory concentration were shown in Table 1.

Reference compounds

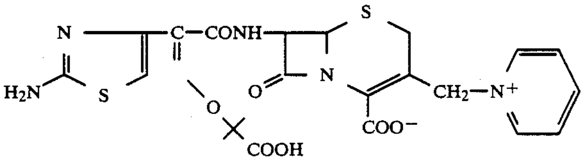

[Ceftazidime]

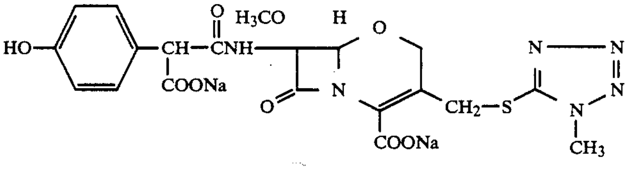

[Moxalactam]

Invented compounds (Ia): Sodium 7-[(Z)-2-(2-aminothiazol-4-yl)-2-(2-furfuryl-oxyimino)-acetamido]-3-acetoxymethyl-3-cephem-4-carboxylate

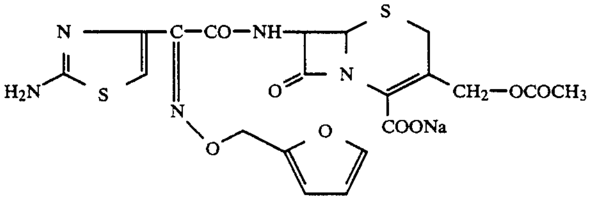

(Ib): 7-[(Z)-2-(2-Aminothiazol-4-yl)-2-(2-furfuryl-oxyimino)-acetamido]-3-(1-pyridiniummethyl)-3-cephem-4-carboxylate -continued

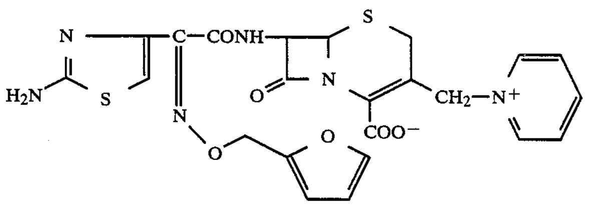

(Ic): Sodium 7-[(Z)-2-(2-aminothiazol-4-yl)-2-(2-furfuryl-oxyimino)-acetamido]-3[(1-methyl-1H-tetrazol-5-yl)-thiomethyl]-3-cephem-4-carboxylate

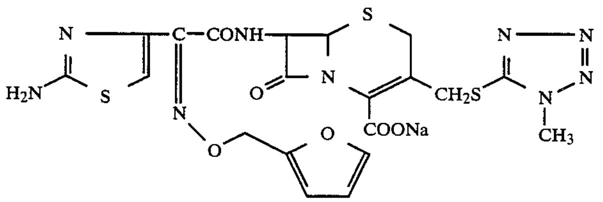

TABLE 1

Comparison of the minimal inhibitory concentration (MIC, μg/ml) of test compounds

| Microorganism | Test compound: Invented compound Ia | Ib | Ic | Reference compound Ceftazidime | Moxalactam |
|---|---|---|---|---|---|
| *Staphylococcus aureus* ATCC 10537 | 1 | 0.25 | 1 | 4 | 4 |
| *Bacillus subtilis* ATCC 6633 | 0.5 | 0.25 | 0.5 | 16 | 8 |
| *Klebsiella pneumoniae* ATCC 10031 | <0.03125 | 0.0625 | <0.0315 | 0.125 | 0.25 |
| *Escherichia coli* ATCC 10536 | 0.5 | 0.5 | 0.5 | 0.125 | 0.125 |
| *Proteus mirabilis* ATCC 25933 | 0.125 | 0.5 | 0.25 | 0.0625 | 0.25 |
| *Salmonella typhimurium* ATCC 14028 | 2 | 2 | 2 | 0.25 | 0.25 |
| *Serratia marcescens* ATCC 27117 | 1 | 0.5 | 1 | 0.0625 | 0.125 |
| *Pseudomonas aeruginosa* ATCC 25619 | 1 | 1 | 1 | 1 | 8 |
| *Pseudomonas aeruginosa* ATCC 27853 | 16 | 8 | 16 | 2 | 16 |
| *Pseudomonas aeruginosa* ATCC 10145 | 16 | 8 | 16 | 2 | 32 |
| *Enterobacter aerogenes* ATCC 29751 | 16 | 4 | 8 | 4 | 1 |

As described in Table 1, the invented compounds (Ia), (Ib) and (Ic) are almost equally active against gram-negative bacteria including *Pseudomonas aeruginosa* as compared with ceftazidime and moxalactam, but they show superior antimicrobiral activities against gram-positive bacteria, especially, *Staphylococcus aureus* and *Bacillus subtilis*. Therefore, the invented compounds have a broad antibacterial spectrum in comparison with the reference compounds.

The pharmacokinetics of the invented compound (Ib) was studied in rat (Fischer, 6~10 weeks). The compound (Ib) was dissolved in phosphate bupper solution(0.05M; pH=9) and intraveneouly administered in a dose of 14.29 mg/kg to four rats, and blood samples from the rats were taken at 1, 5, 10 and 30 mins and 1, 2, 3, 5 and 7 hours after administration of the compound (Ib), respectively.

The concentrations in plasma were measured by HPLC analysis of blood samples, and the results of average concentrations in plasma were listed in Table 2.

The parameters of the pharmacokinetics which were derived from Table 2 were summarized in Table 3.

TABLE 2

Concentration in plasma in rat after administration (14.29 mg/kg) of Compound (Ib)

| Time | 1 min | 5 min | 10 min | 30 min | 1 hr | 2 hr | 3 hr | 5 hr | 7 hr |
|---|---|---|---|---|---|---|---|---|---|
| Concentration in plasma | 111.6 | 60.6 | 43.0 | 20.7 | 12.6 | 6.1 | 4.3 | 1.6 | 0.9 |

(μg/ml)

TABLE 3

| Parameters | Ib | Cefotaxime[1] | Ceftazidime[2] | Ceftriaxone[2] | Ceftriaxone[2] |
|---|---|---|---|---|---|
| Pharmacokinetic parameters of the compound (Ib), cefotaxime, ceftazidime and ceftriaxone intravenously administered | | | | | |
| Species | Rat (Fischer) | Rat (SD) | Dog (Beagle) | Dog (Beagle) | Monkey (Rhesus) |
| Dose (mg/kg) | 14.29 | 20 | 20 | 20 | 20 |
| Model type | | | II Compartment | | |
| $T_{\frac{1}{2}}$ ($\alpha$) (min.) | 6.21 | 4.55 | 7.27 | 6.80 | 23.16 |
| $T_{\frac{1}{2}}$ ($\beta$) (min.) | 95.0 | 14.8 | 49.0 | 50.7 | 204 |
| AUC ($\mu$g · h/ml) | 62.4 | 13.5 | 93.0 | 84.3 | 838 |

<Note>
(1)Chemotheraphy, 28, 1184 (1980) Jpn.
(2)Antimicrob. Agent. Chemotheraphy., 26, 204 (1984).

As described in Table 3, $T_{\frac{1}{2}}(\beta)$ of the invented compound(Ib) in rat is 6.4 times as long as cefotaxime in rat, and 1.9 times as long as ceftazidime or ceftriaxone in dog. Also the compound (Ib) exceeds cefotaxime in AUC by 6.5 times, it shows that the compound(Ib) is very effective in vivo.

The compounds of the formula(I), as active ingredients, may be formulated into pharmaceutical compositions such as oral, form injection form or a mixed form with other pharmaceutically acceptable solid or liquid carrier when they are to be administered to human beings for the therapeutic treatment or prevention of bacterial infections. The pharmaceutical compositions according to the present invention may include solid forms(e.g. capsules, tablets, or sugar-coated pills) or liquid forms(e.g. solution, suspension or emulsion). If desired, supporting agents, stabilizing agents, wetting agents, emulsifying agents and other conventional additives may also be incorporated into the pharmaceutical compositions of this invention.

The dose of the compound in this invention is generally 1~100 mg/kg, preferably 5~50 mg/kg, depending upon the age of the patient, condition of the patient, kind of infection, grade of infection, or used active ingredient.

PREPARATION 1

Furfuryl chloride (VII)

To a solution of freshly distilled furfuryl alcohol (46.20 g, 0.47 moles) in dried ethyl ether(50 ml), dried pyridine(44.70 g, 0.57 moles) was added. The flask was cooled in an ice-bath. When the temperature fell to about 0° C., freshly distilled thionyl chloride (61.70 g, 0.52 moles) dissolved in dried ethyl ether (50 ml) was added at such a rate that the reaction temperature was maintained below 9° C. for thirty minutes. After all of the thionyl chloride had been added, the mixture was stirred for an additional thirty minutes at 4° C. The precipitate was filtered off, and washed with dried ethyl ether (50 ml) twice. The ethereal solution was combined, and the ethyl ether was distilled off at atmospheric pressure. The brown oily residue was distilled in vacuo to give the title compound (35.59 g); b.p. 48°~49° C./26 mmHg.

PREPARATION 2

Ethyl (Z)-2-[2-(triphenylmethyl)aminothiazol-4-yl]-2(2-furfuryl-oxyimino)acetate Ethyl (Z)-2-[2-(triphenylmethyl)aminothiazol-4-yl]-2-(hydroxyimino) acetate (60.20 g, 0.13 moles) was suspended in tetrahydrofuran (600 ml), and then sodium hydroxide (16.01 g, 0.40 moles) and potassium iodide (43.64 g, 0.26 moles) were added. Freshly distilled furfuryl chloride(22.72 g, 0.20 moles) dissolved in dried ethyl ether (20 ml) was added over a period of one minute, and the mixture was further stirred for two hours at room temperature. To the reaction mixture, ethyl ether (800 ml) was added. The ethereal solution was washed with distilled water(500 ml) three times and was dried over anhydrous magnesium sulfate. The filtered ethereal solution was concentrated under reduced pressure, and the residue was chromatographed on a column of silica gel(1000 g). Elution with a 1:4 (v/v) mixture of ethyl acetate/n-hexane gave the title compound(38.19 g) as a pale yellow foam, yield 54%; TLC Rf=0.39(ethyl acetate/n-hexane=$\frac{1}{4}$, v/v); NMR $\delta$ ($CDCl_3$), 1.27 (3H, t, J=7 Hz, $CH_3$), 4.32(2H, q, J=7 Hz,$OCH_2$—$CH_3$), 5.19 (2H, s, =N—O—$CH_2$—), 6.28~6.44 and 7.34~7.40(3H, M, H of the furan), 6.49(1H, s, H of the thiazol), 6.95 (1H, bs, HN), 7.30(15H, s, $(C_6H_5)_3C$—).

PREPARATION 3

Sodium (Z)-2-[2-(triphenylmethyl)aminothiazol-4-yl]-2-(2-furfuryl-oxyimino) acetate Ethyl (Z)-2-[2-(triphenylmethyl)aminothiazol-4-yl]-2-(2-furfuryloxyimino) acetate (10.74 g, 0.02 mole) was dissolved in a mixture of ethyl alcohol(50 ml) and tetrahydrofuran(10 ml). 5N sodium hydroxide solution (aq. 12.3 ml) was added therein, and then the mixture was stirred for three hours at room temperature. The precipitate was collected by filtration, and washed with ethyl alcohol(30 ml) and ethyl ether(30 ml). The filtered cake was dried in vacuo to give the title compound(10.20 g) as a white solid, yield 96%; NMR $\delta$ (MeOH-$d_4$), 5.11 (2H, s,=N—O—$CH_2$—), 6.38~6.60 and 7.51~7.58(3H, m, H of the furan), 6.71(1H, s, H of the thiazol), 7.38(15H, m, $(C_8H_5)_3C$—).

EXAMPLE 1

7-{(Z)-2-[2-(Triphenylmethyl)aminothiazol-4-yl]-2-(2-furfuryloxyimino)-acetamido}-3-acetoxymethyl-3-cephem-4-carboxylic acid Sodium (Z)-2-[2-(triphenylmethyl)aminothiazol-4-yl]-2-(2-furfuryloxyimino)acetate (530 mg, 1.0 mmole) was suspended dried N, N-dimethylformamide (6 ml), and triethylamine (120 mg, 1.2 mmoles) was added thereto. The mixture was cooled in an ice-bath, and then 2-mesitylenesulfonyl chloride (240 mg, 1.1 mmoles) was added. After stirred for five minutes in an ice-bath, the mixture was added with a solution of 7-aminocephalosporanic acid (300 mg, 1.1 mmoles) in a mixture of triethylamine(240 mg, 2.4 mmoles) and N, N-dimethylformamide (4 ml), and stirred at room temperature for three hours. The mixture was diluted with ethyl acetate (30 ml) and washed with 1% hydrochloric acid (20 ml), water(30 ml) and saturated sodium chloride solution(30 ml), successively. The organic phase was dried over anhydrous magnesium sulfate, and the filtered solution was concentrated under reduced pressure. The residue was recrystallized with methyl alcohol to give the title compound(502 mg) as off-white solid, yield 66%; NMR δ (acetone-$d_6$), 2.03 (3H, s, —$OCOCH_3$), 3.42 and 3.70 (2H, ABq, J=18 Hz, —S—$CH_2$—), 4.80 and 5.13 (2H, ABq, J=13 Hz, —$CH_2$ —OCO—), 5.09(2H, s, =NO—$CH_2$—), 5.16(1H, d, J=5 Hz, H in the 6-position), 5.86(1H, dd, J=5 Hz, 9 Hz, H in the 7-position), 6.32~6.52 and 7.50~7.57(3H, m, H of the furan), 6.78(1H, s, H of the thiazol), 7.20~7.50(15H, m, $(C_6H_5)_3C$—), 8.40(1H, d, J=9 Hz, —CONH—); Mass(FAB), $M+1=764$.

EXAMPLE 2

7-[(Z)-2-(2-Aminothiazol-4-yl)-2-(2-furfuryloxyimino)acetamido]-3-acetoxymethyl-3-cephem-4-carboxylic acid (Ia)

To a 7-{(Z)-2-[2-(triphenylmethyl)aminothiazol-4-yl]-2-(2-furfuryloxyimino)-acetamido}-3-acetoxymethyl-3-cephem-4-carboxylic acid (500 mg, 0.66 mmoles) was added cold formic acid (5 ml). The mixture was stirred at room temperature for five hours. The nonsoluble by-product was filtered off and washed with formic acid (3 ml), and the combined filtrate was concentrated under reduced pressure. The residue was chromatographed on a column of silica gel(50 g). Elution with a 1:9 (v/v) mixture of water/acetonitrile gave the title compound (330 mg) as a white crystalline powder, yield 97%; m.p. 250° C. (decompose); TLC Rf=0.72 (water/acetonitrile=1/9, v/v); IR($cm^{-1}$, KBr), 1767, 1682, 1647; NMR δ ($D_2O/NaHCO_3$), 2.12(3H, s, —$OCOCH_3$), 3.29 and 3.65(2H, ABq, J=18 Hz, —S—$CH_2$—), 4.70 and 4.90 (2H, ABq, J=12 Hz, —$CH_2$—OCO—), 5.14 (1H, d, J=5 Hz, H in the 6-position), 5.20(2H, s,=N—O—$CH_2$—), 5.78(1H, d, J=5 Hz, H in the 7-position), 6.46~6.66 and 7.56~7.60(3H, m, H of the furan), 7.04(1H, s, H of the thiazol); Mass(-FAB), $M+1=522$.

EXAMPLE 3

7-[(Z)-2-(2-Aminothiazol-4-yl)-2-(2-furfuryloxyimino)acetamido]-3-(1-pyridiniummethyl)-3-cephem-4-carboxylate(Ib)

Sodium (Z)-2-[2-(triphenylmethyl) aminothiazol-4-yl]-2-(2-furfuryloxyimino)acetate (530 mg, 1.0 mmole) was suspended in dried N,N-dimethylformamide(6 ml), and triethylamine(180 mg, 1,8 mmoles) was added. The mixture was cooled in an ice-bath, and then 2-mesitylenesulfonyl chloride (240 mg, 1.1 mmoles) was added. After stirred for five minutes in an ice-bath, the mixture was added with the solution of 7-amino-3-(1-pyridiniummethyl)-3-cephem-4-carboxylate dihydrochloride(360 mg, 1.1 mmoles) in a mixture of triethylamine (300 mg, 3.0 mmoles) and N,N-dimethylformamide (4 ml). The mixture was triturated with ethyl ether (30 ml). The precipitate was collected by filtration, washed with ethyl ether (10 ml), and dried to give a crude 7-{(Z)-2-[2-(triphenylmethyl)aminothiazol4-yl-2-(2-furfuryl-oxyimino)-acetamido}-3-(1-pyridiniummethyl)-3-cephem4-carboxylate. This compound was added in cold formic acid (5 ml). The mixture was stirred at room temperature for five hours. The nonsoluble by-product was filtered off, and the filtrate was concentrated under reduced pressure. The residue was chromatographed on a column of silica gel (50 g). Elution with a 1:9 (v/v) mixture of water/acetonitrile gave the title compound(380 mg) as a off-white powder, yield 57%; m.p. 275° C.(decompose); TLC Rf=0.37(water/acetonitrile=¼, v/v); IR ($cm^{-1}$, KBr), 1768, 1668, 1612; NMR δ ($D_2O$), 3.05 and 3.61(2H, ABq, J=18 Hz, —S—$CH_2$—), 5.20 (2H, s,=N—O—$CH_2$—), 5.24 (1H, d, J=5 Hz, H in the 6-position), 5,33 and 5.59(2H, ABq, J=14 Hz, —$CH_2$—N—), 5.80(1H, d, J=5 Hz, H in the 7-position), 6.40~6.60 and 7.40~7.50 (3H, m, H of the furan), 7.00(1H, s, H of the thiazol), 8.00~9.00 (5H, m, H of the pyridine); Mass (FAB), $M+1=541$.

EXAMPLE 4

Sodium 7-[(Z)-2-(2-aminothiazol-4-yl)-2-(2-furfuryloxyimino)-acetamido]-3-[(1-methyl-1H-tetrazol-5-yl) thiomethyl]-3-cephem-4-carboxylate(Ic)

Sodium (Z)-2-[2-(triphenylmethyl)aminothiazol-4-yl]-2-(2-furfuryloxyimino) acetate (530 mg, 1.0 mmole) was suspended in dried N,Ndimethylformamide(6 ml), and triethylamine(150 mg, 1.5 mmoles) was added. The mixture was cooled in an ice-bath, and then 2-mesitylenesulfonyl chloride(218 mg, 1.0 mmole) was added. After stirred for five minutes in an ice-bath, the mixture was added with the solution of 7-amino-3-[1-methyl-1H-tetrazol-5yl)thiomethyl]-3-cephem-4-carboxylic acid (400 mg, 1.3 mmoles) in a mixture of the triethylamine (300 mg, 3.0 mmoles) and N,N-dimethylkformamide(4 ml). The mixture was stirred at room temperature for ninety minutes. The mixture was triturated with ethyl ether (30 ml). The precipitate was collected by filtration, washed with ethyl ether (10 ml), and dried to give a crude 7-{(Z)-2-[2-(triphenylmethyl)aminothiazol-4-yl]-2-(2-furfuryl-oxyimino)-acetamido}-3-[(1-methyl-1H-tetrazol-5-yl)thiomethyl]-3-cephem-4-carboxylic acid. This compound was added in cold formic acid (5 ml). The mixture was stirred at room temperature for three hours. The non-soluble byproduct was filtered off, and the filtrate was concentrated under reduced pressure. To this residue was added sodium acetate(90 mg, 1.1 mmoles) and acetone(10 ml), and the mixture was stirred at room temperature for an hour. The precipitate was filtered, and the filtered cake was chromatographed on a column of silica gel (50 g). Elution with a 1:6 (v/v) mixture of water/acetonitrile gave the title compound (275 mg) as a white powder, yield 46%; m.p. 275° C. (decompose); TLC Rf=0.49(water-/acetonitrile=1/6, v/v); IR ($cm^{-1}$, KBr), 1765, 1678, 1620; NMR δ ($D_2O$), 3.38 and 3.80 (2H, ABq, J=17 Hz, —S—$CH_2$— in the 2-position), 4.04 H, s, N—$CH_3$), 4.06 and 4.35(2H, Abq, J=13 Hz, —$CH_2$—S— in the 3-position), 5.16(1H, d, J=5 Hz, H in the 7-position), 5.21(2H, s, =N—O—$CH_2$—), 5.75(1H, d, J=5 Hz, H in the 7-positon), 6.38~6.64 and 7.52~7.62(3H, m, H of the furan), 7.03(1H, s, H of the thiazol); Mass (FAB), $M+1=600$.

EXAMPLE 5

7-[(Z)-2-(2-Aminothiazol-4-yl)-2-(2-furfuryloxyimino)acetamido]-3-(1-pyridiniummethyl)-=3-cephem-4-carboxylate(Ib)

Sodium (Z)-2-[2-(triphenylmethyl)aminothiazol-4-yl]-2-(2-furfuryloxyimino) acetate (5.68 g, 10.7 mmoles)

was suspended in ethyl acetate (100 ml), 0.2N Hydrochloric acid (aq, 107 ml) was added, and the mixture was stirred at room temperature until the solid was completely dissolved. The organic layer was seperated, washed with water(100 ml), and dried over anhydrous magnesium sulfate. The filtered solution was concentrated to give (Z)-2-[2-(triphenylmethy)aminothiazol-4-yl]-2-(2-furfuryloxyimino)acetic acid (5.13 g, m.p. 116° C., decompose). Above compound was dissolved in dried methylene chloride (25 ml), the mixture was cooled to −15° C. Phosphorous pentachloride (2.31 g, 11.1 mmoles) was added to the mixture and then the resultant mixture was stirred at −15° C. for an hour. The mixture was triturated with isopropyl ether(100 ml) at −10° C. The precipitate was filtered, and dried in vacuo to give (Z)-2-[2-(triphenylmethyl)aminothiazol-4-yl]-2-(2-furfuryl-oxyimino) acetyl chloride hydrochloride (4.55 g, 80%). To the above acid chloride (296 mg, 0.52 mmoles) was added 7-amino-3-(1-pyridiniumemethyl)-3-cephem-4-carboxylate dihydrochloride (200 mg, 0.55 mmoles), methylene chloride(6 ml) and triethylamine (0.42 ml, 3.0 mmoles). The mixture was stirred at 4° C. for thirty minutes. The mixture was washed with water(5 ml), and dried over anhydrous magnesium sulfate. The filtered solution was concentrated in vacuo. The residue was dissolved in N,N-dimethylformamide(91 ml) and triturated with ethyl acetate (20 ml). The precipitate was collected and dried in vacuo. After this compound was dissolved in cold formic acid (0.5 ml), the mixture was stirred at room temperature for five hours, and triturated with ethyl ether(10 ml). The precipitate was collected and chromatographed on a column of silica gel(30 g). Elution with a 1:4 (v/v) mixture of water/acetonitrile gave the same compound (129 mg) as the title compound yield 48%; m.p. 275° C.(decompose); TLC Rf=0.37(water/acetonitrile=¼, v/v); IR (cm$^{-1}$, KBr), 1768, 1668, 1612: NMR δ ($D_2O$), 3.05 and 3.61(2H, ABq, J=18 Hz, —S—$CH_2$—), 5.20 (2H, s,=N—O—$CH_2$—), 5.24 (1H, d, J=5 Hz, H in the 6-position), 5.33 and 5.59 (2H, ABq, J=14 Hz, —$CH_2$—N—), 5.80(1H, d, J=5 Hz, H in the 7-positon), 6.40~6.60 and 7.40~7.50 (3H, m, H of the furan), 7.00(1H, s, H of the thiazol), 8.00~9.00 (5H, m, H of the pyridine); Mass (FAB), $M+1=541$.

We claim:

1. A cephalosporin compound of the formula

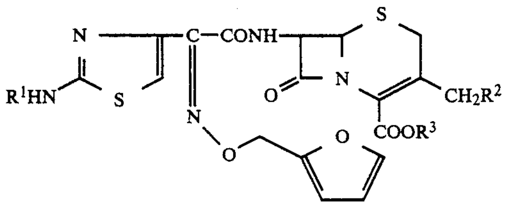

(I)

wherein $R^1$ is a hydrogen atom or an amino protecting group; $R^2$ is acetoxy, 1-pyridinium or (1-methyl-1H-tetrazol-5-yl)thio; and $R^3$ is a hydrogen atom, a sodium or potassium ion, or a carboxyl protecting group; and a pharmaceutically acceptable salt or ester thereof.

2. The compound of claim 1 wherein said amino protecting group is acyl, ar(lower)alkyl, ar(lower)alkyl substituted with a $C_1$–$C_3$ alkoxy group, halo(lower)alkyl, tetrahydropyranyl, phenylthio, alkylidene, aralkylidene or cyclolidene.

3. The compound of claim 2, wherein said acyl is $C_1$~$C_6$ alkoxycarbonyl, lower alkanesulfonyl, arenesulfonyl, aroyl, ar(lower) alkanoyl or ar(lower)alkoxy carbonyl.

4. The compound of claim 2 wherein said acyl may be further substituted with 1~3 substituents such as halogen, hydroxy, cyano or nitro.

5. The compound of claim 1 wherein $R^2$ is acetoxy, 1-pyridinium, or (1-methyl-1H-tetraxol-5-yl)thio.

6. The compound of claim 1 wherein said carboxyl protecting group is lower alkyl ester, lower alkenyl ester, lower alkoxy(lower)alkyl ester, lower alkylthio(-lower)alkyl ester, halo(lower)alkyl ester, benzyl p-nitrobenzyl, p-methoxybenzyl or trimethylsilyl.

7. The compound of claim 1 wherein said cephalosporin compound include the 2-imino thiazolin-4-yl forms as tautomers.

8. A pharmaceutical composition, which comprises the cephalosporin compounds of the formula (I) as an active ingredient, in association with a pharmaceutically acceptable carrier

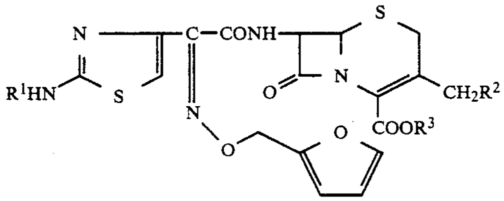

(I)

wherein $R^1$ is a hydrogen atom or an amino protecting group;

$R^2$ is acetoxy, 1-pyridinium or (1-methyl-1H-tetrazol-5-yl)thio; and $R^3$ is a hydrogen atom, a sodium or potassium ion, or a carboxyl protecting group; and a pharmaceutically acceptable salt or ester thereof.

* * * * *